United States Patent
Cui et al.

(10) Patent No.: US 11,406,770 B2
(45) Date of Patent: Aug. 9, 2022

(54) CIRCULATION PIPELINE FOR INTRACAVITY HYPERTHERMIC PERFUSION

(71) Applicant: GUANGZHOU BRIGHT MEDICAL TECHNOLOGY CO., LTD., Guangzhou (CN)

(72) Inventors: Shuzhong Cui, Guangzhou (CN); Diwen Huang, Guangzhou (CN); Hongsheng Tang, Guangzhou (CN); Yunhua Tang, Guangzhou (CN); Bin Wang, Guangzhou (CN); Qiang Ruan, Guangzhou (CN); Jing Li, Guangzhou (CN)

(73) Assignee: GUANGZHOU BRIGHT MEDICAL TECHNOLOGY CO., LTD., Guangzhou (CN)

( * ) Notice: Subject to any disclaimer, the term of this patent is extended or adjusted under 35 U.S.C. 154(b) by 172 days.

(21) Appl. No.: 16/954,017

(22) PCT Filed: Jul. 27, 2018

(86) PCT No.: PCT/CN2018/097599
§ 371 (c)(1),
(2) Date: Jun. 15, 2020

(87) PCT Pub. No.: WO2019/205326
PCT Pub. Date: Oct. 31, 2019

(65) Prior Publication Data
US 2021/0077749 A1  Mar. 18, 2021

(30) Foreign Application Priority Data
Apr. 28, 2018 (CN) .......................... 201810401888.8

(51) Int. Cl.
*A61M 5/44* (2006.01)
*A61M 5/142* (2006.01)
(Continued)

(52) U.S. Cl.
CPC ............ *A61M 5/445* (2013.01); *A61M 5/142* (2013.01); *A61M 5/16881* (2013.01);
(Continued)

(58) Field of Classification Search
CPC .. A61M 2210/1085; A61M 2205/3337; A61M 2205/3368; A61M 2205/368;
(Continued)

(56) References Cited

FOREIGN PATENT DOCUMENTS

| CN | 202313910 | 7/2012 |
|---|---|---|
| CN | 202892196 U | 4/2013 |

(Continued)

OTHER PUBLICATIONS

Ba Mingchen et al.,"Bladder intracavitary hyperthermic perfusion chemotherapy for the prevention of recurrence of non-muscle invasive bladder cancer after transurethral resection,"OncologyReports,vol. 37,No. 5,May 11, 2017, ages2761-2770.*

(Continued)

*Primary Examiner* — Jason E Flick
(74) *Attorney, Agent, or Firm* — Seyfarth Shaw LLP

(57) ABSTRACT

Provided is a circulation pipeline (10) for intracavity hyperthermic perfusion, the circulation pipeline comprising a heating tank (100), a liquid intake pipeline (101), a liquid discharge pipeline (102), a circulating pump (200), a pre-filling pipeline (103), a liquid return pipeline (104), a cavity entry pipeline (105) and a cavity exit pipeline (106), wherein a liquid storage cavity (100a) is formed in the heating tank (100), and the liquid intake pipeline (101) is in communication with the liquid storage cavity (100a). A medicinal (Continued)

liquid enters the liquid storage cavity (100a) of the heating tank (100) through the liquid intake pipeline (101).

9 Claims, 13 Drawing Sheets

(51) Int. Cl.
*A61M 5/168* (2006.01)
*A61M 5/32* (2006.01)

(52) U.S. Cl.
CPC ... *A61M 5/3202* (2013.01); *A61M 2205/3337* (2013.01); *A61M 2205/3368* (2013.01); *A61M 2205/368* (2013.01)

(58) Field of Classification Search
CPC .. A61M 31/00; A61M 5/142; A61M 5/16881; A61M 5/3202; A61M 5/445; A61M 2205/36; A61M 2210/005; A61M 3/0204; A61M 3/0229; A61M 3/0283; A61M 2210/1078; A61M 2205/33; A61M 2205/3331; A61M 5/14; A61M 5/168; A61M 5/16877; A61M 5/44; A61F 7/12; A61F 2007/0069; A61F 2007/0095; A61F 2007/126; A61F 7/00; A61F 2007/59; A61F 2007/63
See application file for complete search history.

(56) References Cited

FOREIGN PATENT DOCUMENTS

| | | |
|---|---|---|
| CN | 203954449 | 11/2014 |
| CN | 205084071 | 3/2016 |
| CN | 105727426 | 7/2016 |
| CN | 108836618 | 11/2018 |
| JP | 2000296146 | 10/2000 |

OTHER PUBLICATIONS

Supplemental European Search Report for corresponding Application No. 18915831.4 dated May 11, 2021, 9 pages.

Ba Mingchen et al, "Bladder intracavitary hyperthermic perfusion chemotherapy for the prevention of recurrence of non-muscle invasive bladder cancer after transurethral resection," Oncology Reports, vol. 37, No. 5, May 11, 2017, pp. 2761-2770.

International Search Report for Application No. PCT/CN2018/097599, dated Dec. 28, 2018, 3 pages.

Written Opinion for Application No. PCT/CN2018/097599, dated Dec. 28, 2018, 5 pages.

* cited by examiner

CIRCULATION PIPELINE FOR INTRACAVITY HYPERTHERMIC PERFUSION

CROSS REFERENCE TO RELATED APPLICATIONS

This is a U.S. National Stage application of, and claims priority to, PCT/CN2018/097599, filed Jul. 27, 2018, which further claims priority to Chinese Patent Application No. 201810401888.8, filed Apr. 28, 2018, the disclosures of which are incorporated herein by reference in their entirety.

TECHNICAL FIELD

The present disclosure relates to the technical field of medical instruments, and more particularly, to a circulation pipeline for intracavity hyperthermic perfusion.

BACKGROUND

After a tumor is resected or after a palliative surgery, it is necessary to directly perfuse heated normal saline and anticancer drugs into the cavity (such as the thoracic cavity, abdominal cavity, or bladder, etc.) of the patient, so that the anticancer drugs directly and sufficiently contact with tumor tissues or cells to play the role of adjuvant chemotherapy. The basic research of tumor thermotherapy proves that the tumor tissue has thermal sensitivity. The therapeutic liquid is heated by using a hyperthermic perfusion extracorporeal heating device and is introduced into the body cavity of the patient through a circulation pump, and an effective therapeutic temperature is maintained for a certain period of time. In this way, a thermal killing mechanism can be fully exerted, metastatic cancer cells widely planted on the serosa can be killed, the lesions that cause the malignant effusion can be eliminated, and the purpose of effectively treating the cancerous effusion is achieved. During and after surgery, the heated therapeutic liquid is used for heat clearing, so that the diffuse diffusion of cancer cells in the cavity can be prevented.

However, when a conventional circulation pipeline is used for hyperthermic perfusion circulation therapy, air in the pipeline system cannot be exhausted. If too much air enters the body cavity, symptoms such as inflammation may be caused.

SUMMARY

Based on this, in view of the aforementioned technical problems, it is necessary to provide a circulation pipeline for intracavity hyperthermic perfusion capable of exhausting air in the pipeline system in advance to avoid causing inflammation.

A circulation pipeline for intracavity hyperthermic perfusion, including:

a heating tank, the heating tank being hollow to form a liquid storage cavity, the liquid storage cavity being configured to store a medicinal solution;

a liquid inlet pipeline, one end of the liquid inlet pipeline being in communication with the liquid storage cavity, and the other end of the liquid inlet pipeline being configured to be in communication with a medicinal solution bag;

a liquid outlet pipeline, one end of the liquid outlet pipeline being in communication with the liquid storage cavity;

a circulation pump connected in series to the liquid outlet pipeline and configured to extract the medicinal solution in the liquid storage cavity;

a pre-filling pipeline, one end of the pre-filling pipeline being in communication with the other end of the liquid outlet pipeline;

a liquid return pipeline, one end of the liquid return pipeline being in communication with the other end of the pre-filling pipeline, and the other end of the liquid return pipeline being in communication with the liquid storage cavity;

a cavity inlet pipeline, one end of the cavity inlet pipeline being in communication with the other end of the liquid outlet pipeline, and the other end of the cavity inlet pipeline being in communication with a body cavity; and a cavity outlet pipeline, one end of the cavity outlet pipeline being configured to be in communication with the body cavity, the other end of the cavity outlet pipeline being in communication with one end of the liquid return pipeline, and the pre-filling pipeline being connected in parallel with the cavity inlet pipeline and the cavity outlet pipeline.

The aforementioned circulation pipeline for intracavity hyperthermic perfusion has at least the following advantages:

When in use, the medicinal solution enters the liquid storage cavity of the heating tank through the liquid inlet pipeline. When the amount of the medicinal solution in the heating tank reaches a set value, the liquid inlet pipeline is closed, and the medicinal solution in the heating tank is pre-heated by an electromagnetic induction heating device until a pre-heating temperature is reached. The medicinal solution is extracted from the liquid storage cavity under the action of the circulation pump, and then flows back to the heating tank through the liquid outlet pipeline, the pre-filling pipeline, and the liquid return pipeline, so that the air in the pipeline system can be exhausted in advance to avoid causing inflammation. Then the medicinal solution is extracted from the liquid storage cavity again under the action of the circulation pump, and then enters the bladder through the liquid outlet pipeline and the cavity inlet pipeline, and then flows out of the bladder, and flows back to the heating tank through the cavity outlet pipeline and the liquid return pipeline.

DETAILED DESCRIPTION OF EMBODIMENTS

In order to make the foregoing objects, features, and advantages of the present disclosure more apparent and intelligible, specific embodiments of the present disclosure are described in detail below with reference to the accompanying drawings. Numerous specific details are set forth in the following description in order to fully understand the present disclosure. However, the present disclosure can be implemented in many other ways than those described herein, and those skilled in the art can make similar improvements without departing from the content of the present disclosure, so the present disclosure is not limited by the specific implementations disclosed below.

It should be noted that when an element is referred to as being "fixed to" another element, it may be directly on the other element or there may be an intermediate element. When an element is considered to be "connected" to another element, it can be directly connected to another element or connected to another element with an intermediate element. These terms "vertical", "horizontal", "left", "right" and similar expressions used herein are for illustrative purposes only and are not meant to be the only implementations.

Unless defined otherwise, all technical and scientific terms used herein have the same meaning as commonly understood by those skilled in the art to which the present disclosure belongs. The terms used in the description of the present disclosure are only for the purpose of describing specific embodiments, and are not intended to limit the present disclosure. The technical features of the embodiments described above can be arbitrarily combined. In order to simplify the description, all possible combinations of the technical features in the above embodiments have not been described. However, as long as there is no contradiction in the combinations of these technical features, all combinations should be considered within the scope of the present description.

Figure 1:
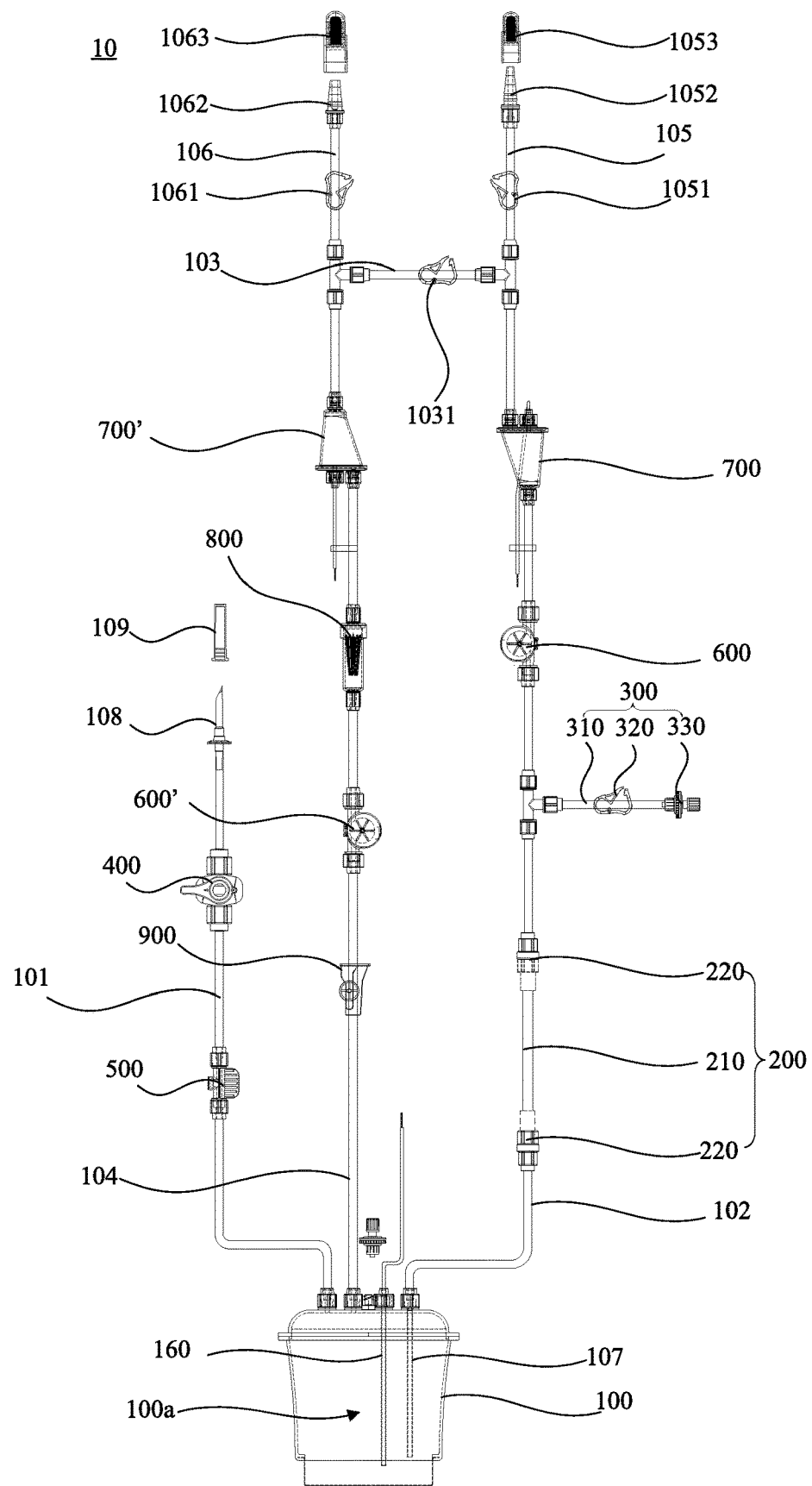
FIG. 1 is a schematic view of a circulation pipeline for intracavity hyperthermic perfusion in accordance with an embodiment.

Referring to FIG. 1, a circulation pipeline for intracavity hyperthermic perfusion 10 in accordance with an embodiment can be applied to a bladder hyperthermic perfusion device to form a circulation pipeline system, and is connected to a urinary catheter placed in the bladder. The circulation pipeline for intracavity hyperthermic perfusion 10 can exhaust air in the pipeline system in advance before treatment to avoid causing inflammation. In addition, the circulation pipeline for intracavity hyperthermic perfusion 10 can be used in conjunction with an electromagnetic induction heating device to enable chemotherapeutic drugs filled into the bladder to be maintained at a set thermotherapy temperature for a long time, thereby achieving a killing effect of the chemotherapeutic drugs and the thermotherapy on superficial bladder tumors. Certainly, in other embodiments, the circulation pipeline for intracavity hyperthermic perfusion 10 can also be applied to the thoracic cavity, abdominal cavity, and rectum for treatment.

Figure 2:
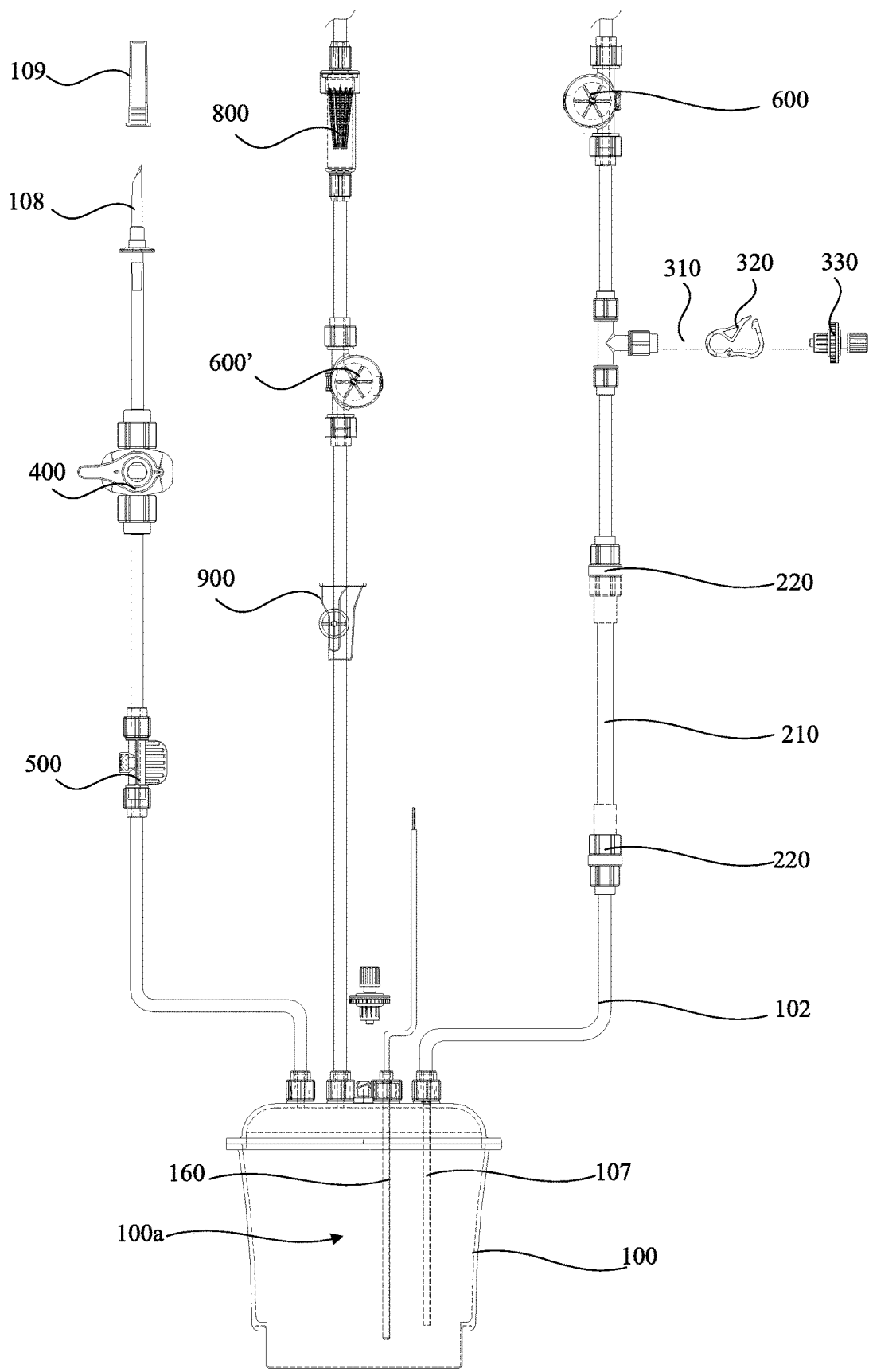
FIG. 2 is a partial schematic view of FIG. 1.
Figure 3:
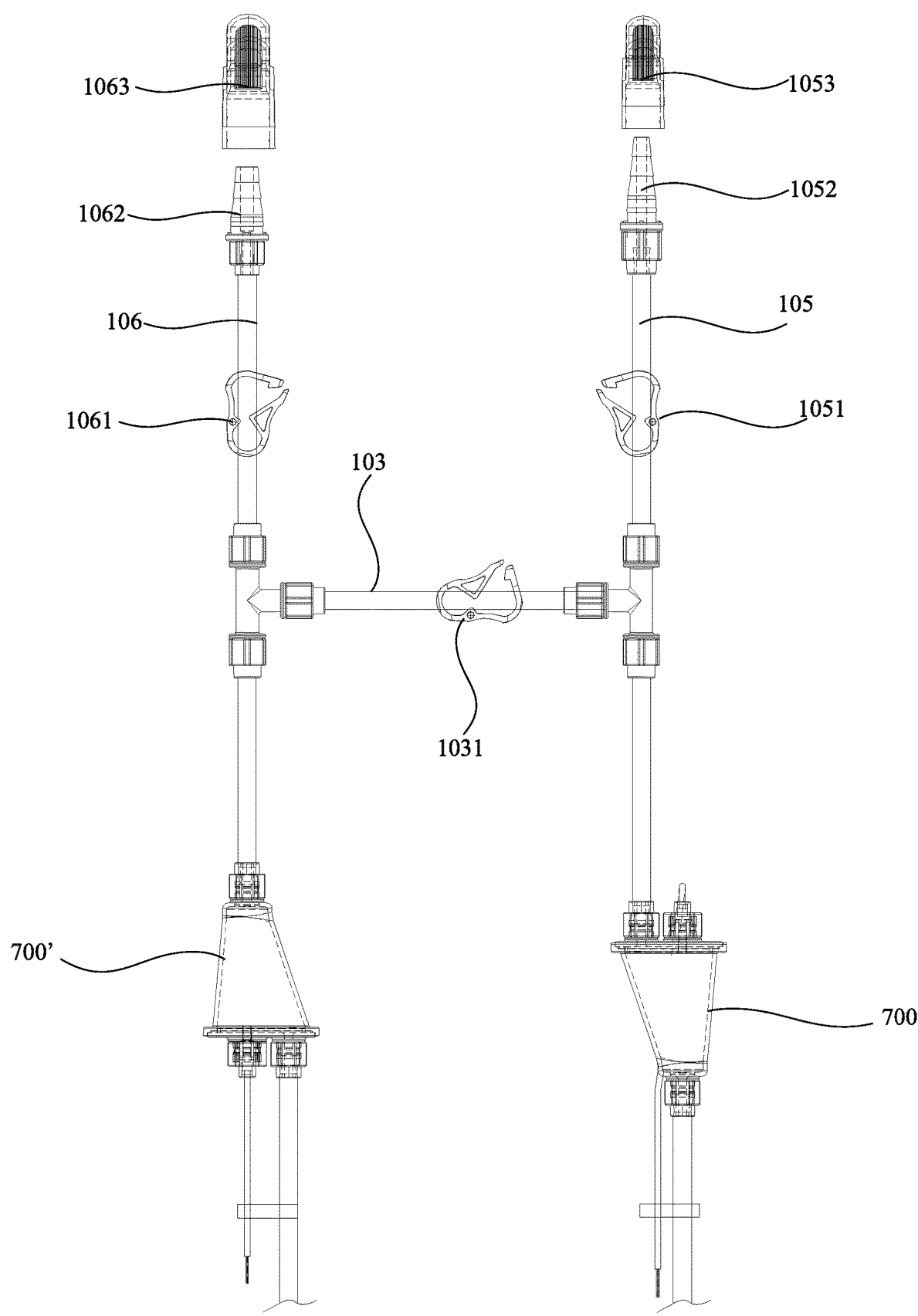
FIG. 3 is another partial schematic view of FIG. 1.

Referring to FIG. 2 and FIG. 3 together, the circulation pipeline for intracavity hyperthermic perfusion 10 includes a heating tank 100, a liquid inlet pipeline 101, a liquid outlet pipeline 102, a circulation pump 200, a pre-filling pipeline 103, a liquid return pipeline 104, a cavity inlet pipeline 105, and a cavity outlet pipeline 106. The heating tank 100 is hollow to form a liquid storage cavity 100a, which is configured to store a medicinal solution. One end of the liquid inlet pipeline 101 is in communication with the liquid storage cavity 100a, and the other end of the liquid inlet pipeline 101 is configured to be in communication with a medicinal solution bag (or a medicinal solution bottle, a medicinal solution tank, etc.). One end of the liquid outlet pipeline 102 is in communication with the liquid storage cavity 100a, and the other end of the liquid outlet pipeline 102 is in communication with one end of the pre-filling pipeline 103 and one end of the cavity inlet pipeline 105. The pre-filling pipeline 103 and the cavity inlet pipeline 105 are arranged in parallel. For example, a pipette 107 may be connected in series to one end of the liquid outlet pipeline 102, the pipette 107 extends into the liquid storage cavity 100a, and one end of the pipette 107 is proximate to a bottom of the heating tank 100 to ensure that the medicinal solution in the heating tank 100 can be smoothly extracted into the liquid outlet pipeline 102.

The circulation pump 200 is connected in series to the liquid outlet pipeline 102, and is configured to extract the medicinal solution in the liquid storage cavity 100a. Specifically, the circulation pump 200 includes a pump pipe 210 and two pump pipe joints 220. The two pump pipe joints 220 are connected to two opposite ends of the pump pipe 210, respectively, and are configured to connect the pump pipe 210 in series to the liquid outlet pipeline 102. The pump pipe 210 is configured to adjust a speed of extracting liquid from the heating tank 100.

One end of the pre-filling pipeline 103 is in communication with the other end of the liquid outlet pipeline 102, and the other end of the pre-filling pipeline 103 is in communication with one end of the liquid return pipeline 104. The pre-filling pipeline 103 is connected in parallel with the cavity inlet pipeline 105 and the cavity outlet pipeline 106. A pre-filling valve 1031 is also connected in series to the pre-filling pipeline 103 and is configured to control opening and closing of the pre-filling pipeline 103. One end of the liquid return pipeline 104 is in communication with the other end of the pre-filling pipeline 103 and the other end of the cavity outlet pipeline 106, and the other end of the liquid return pipeline 104 is in communication with the liquid storage cavity 100a. The liquid return pipeline 104 is capable of allowing the medicinal solution in the bladder discharged through the cavity outlet pipeline 106 to flow back to the heating tank 100. For example, the liquid return pipeline 104, the pre-filling pipeline 103, and the cavity outlet pipeline 106 may be connected together through a T-pipe.

One end of the cavity inlet pipeline 105 is in communication with the other end of the liquid outlet pipeline 102, and the other end of the cavity inlet pipeline 105 is configured to be in communication with the body cavity (the bladder in the present embodiment). The cavity inlet pipeline 105 is capable of introducing the medicinal solution into the bladder. Specifically, a cavity inlet valve 1051 may be connected in series to the cavity inlet pipeline 105 to control the opening and closing of the cavity inlet pipeline 105. A cavity inlet conical head 1052 may also be provided on the other end of the cavity inlet pipeline 105 to facilitate cooperation with a urinary catheter. Optionally, a protection cap 1053 can also be sleeved on the cavity inlet conical head 1052, and is configured to protect the cavity inlet conical head 1052 when not in use, thereby preventing foreign dust or debris from entering the cavity inlet pipeline 105.

One end of the cavity outlet pipeline 106 is configured to be in communication with the body cavity (the bladder in the present embodiment), and the other end of the cavity outlet pipeline 106 is in communication with the liquid return pipeline 104. The pre-filling pipeline 103 is connected in parallel with the cavity inlet pipeline 105 and the cavity outlet pipeline 106. The medicinal solution in the bladder can be discharged by the cavity outlet pipeline 106, and flowed back to the heating tank 100 through the liquid return pipeline 104. Specifically, a cavity outlet valve 1061 may be connected in series to the cavity outlet pipeline 106, and is configured to control opening and closing of the cavity outlet pipeline 106. A cavity outlet conical head 1062 can also be provided on one end of the cavity outlet pipeline 106 to facilitate cooperation with the urinary catheter. Optionally, a protection cap 1063 can also be sleeved on the cavity outlet conical head 1062, and is configured to protect the cavity outlet conical head 1062 when not in use, thereby preventing foreign dust or debris from entering the cavity outlet pipeline 106.

Figure 4:
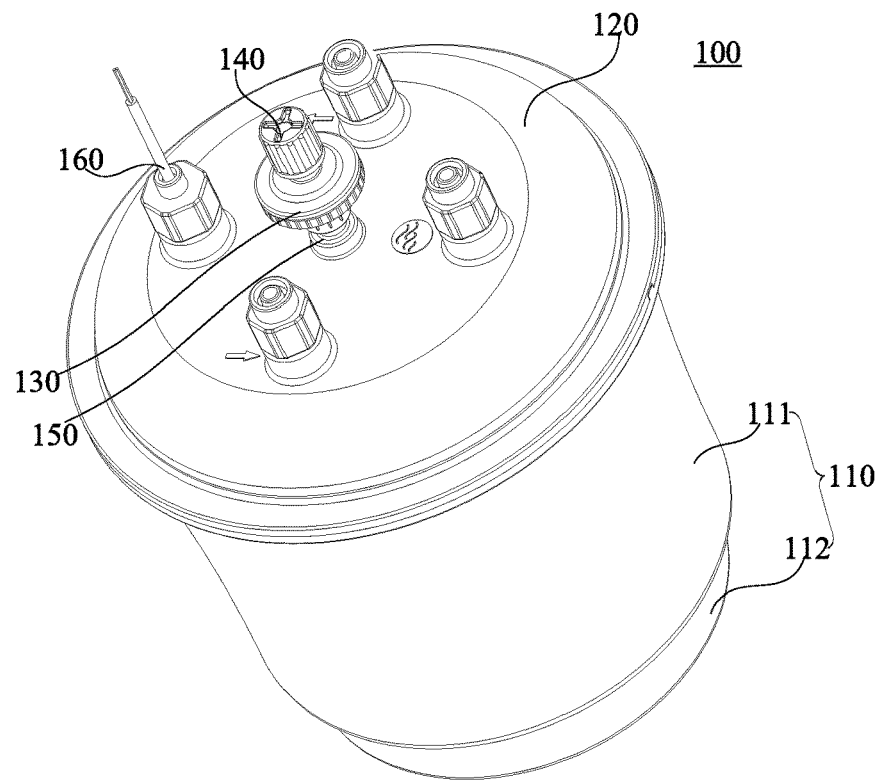
FIG. 4 is a schematic view of a heating tank in accordance with an embodiment.
Figure 5:
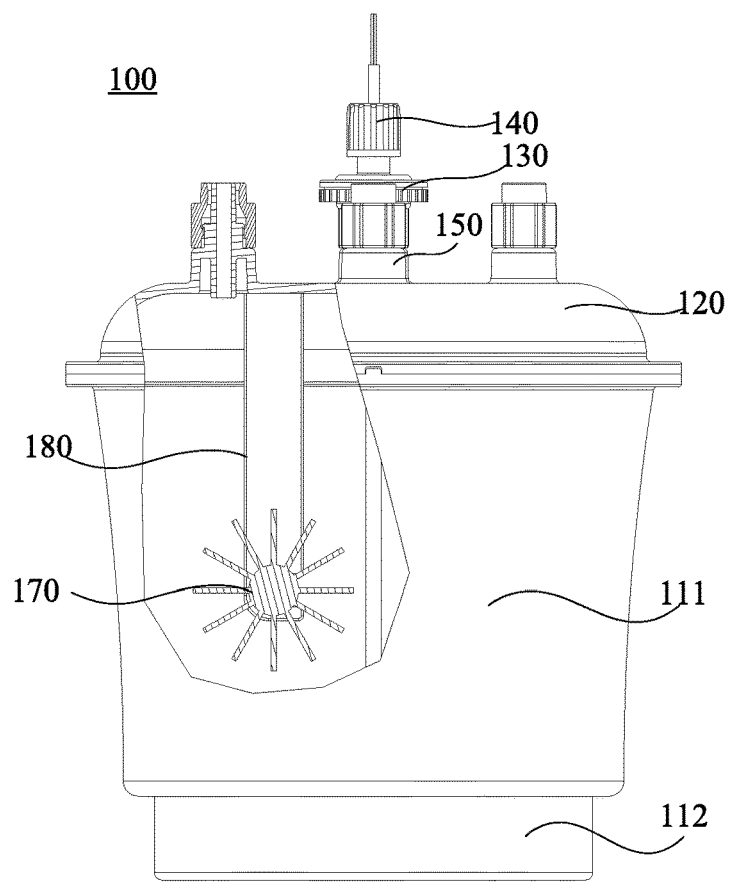
FIG. 5 is a partial sectional view of the heating tank of FIG. 4.
Figure 6:
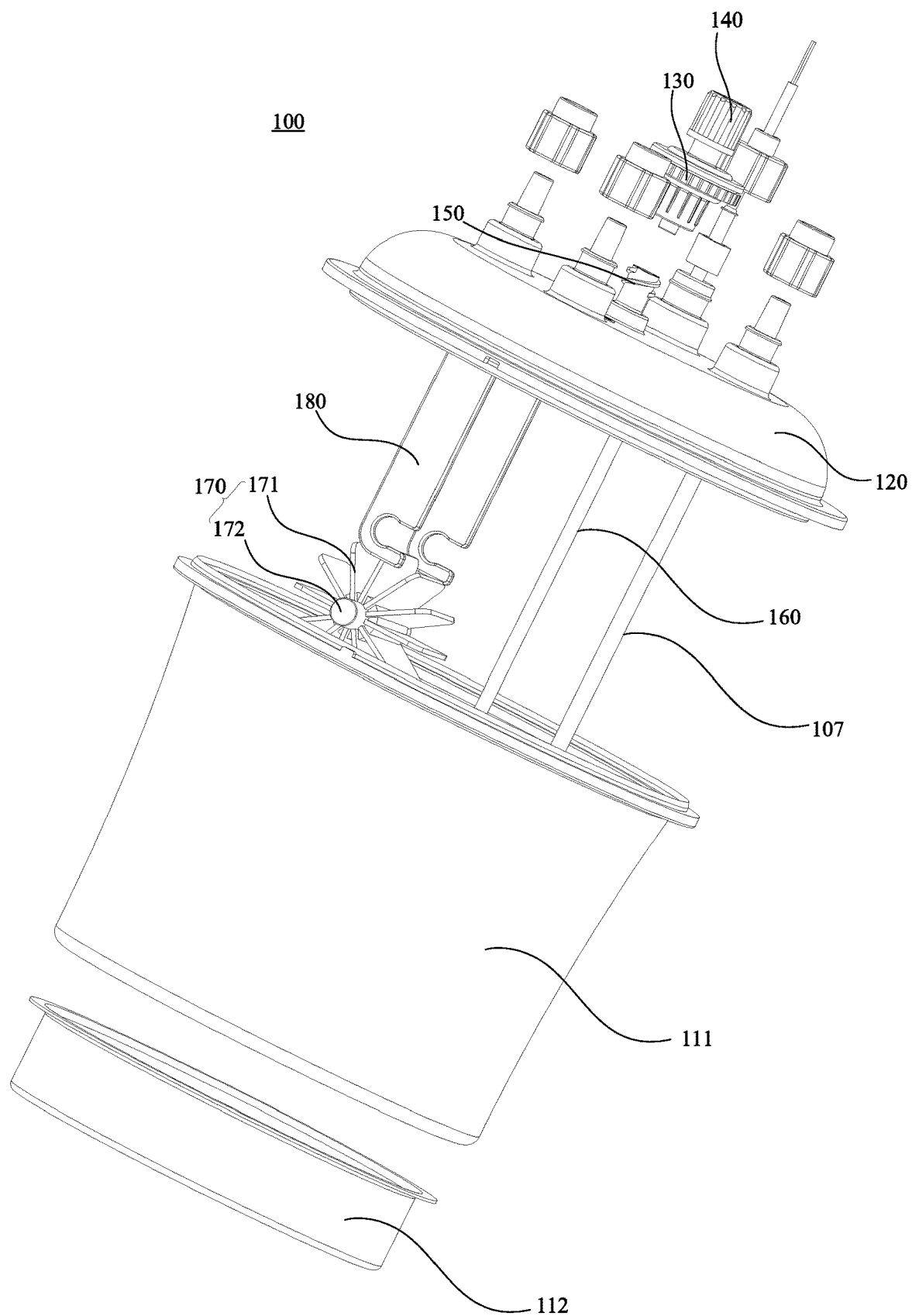
FIG. 6 is a schematic exploded view of the heating tank of FIG. 4.
Figure 7:
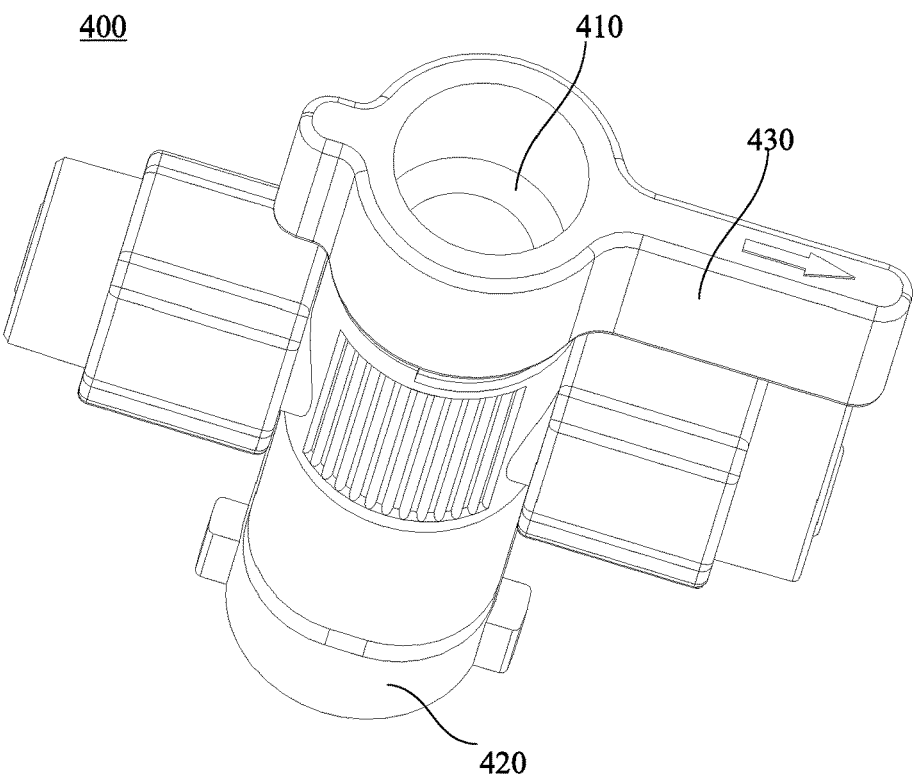
FIG. 7 is a schematic view of a two-way valve in accordance with an embodiment.
Figure 8:
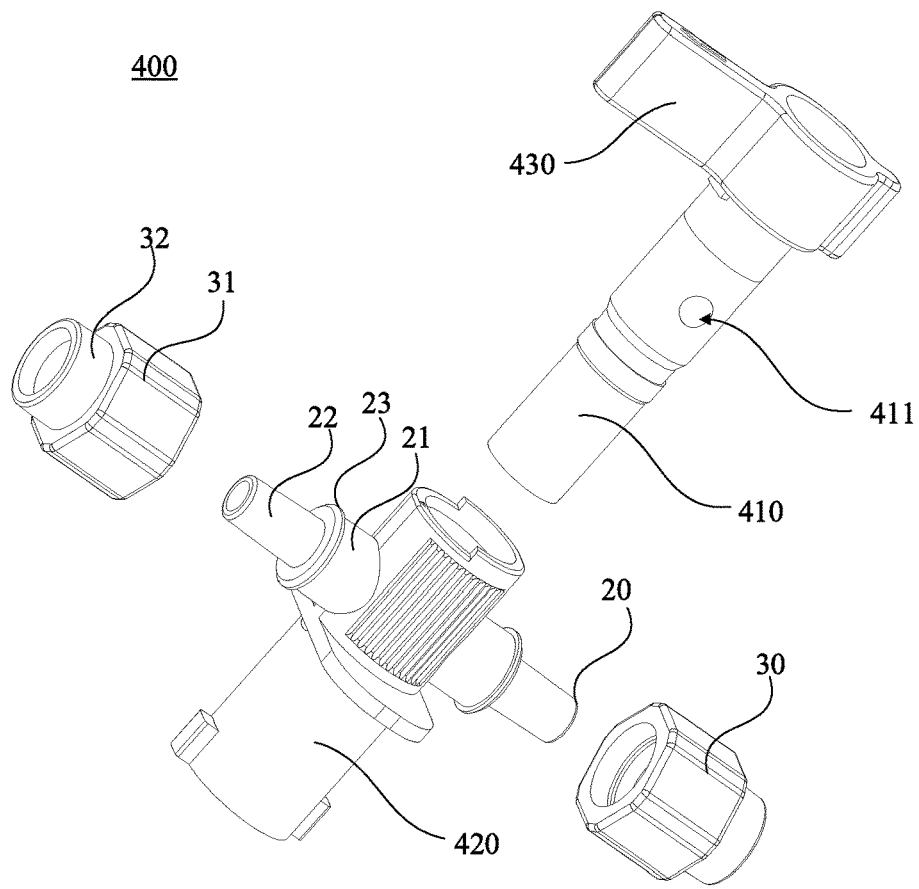
FIG. 8 is a schematic exploded view of the two-way valve of FIG. 7.
Figure 9:
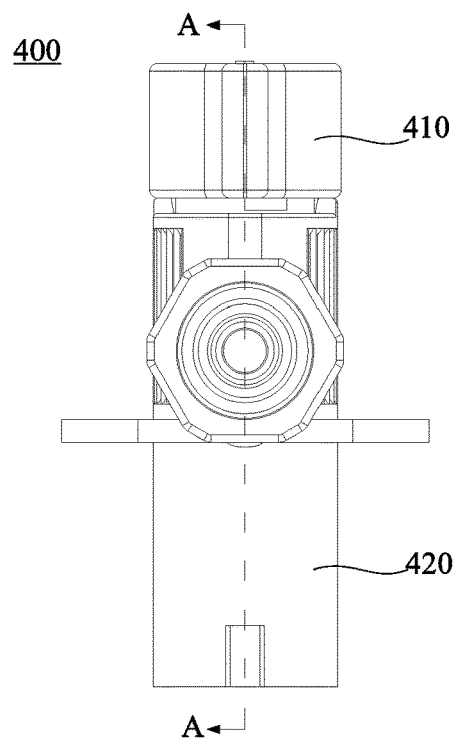
FIG. 9 is a schematic view of the two-way valve of FIG. 7 with another perspective.
Figure 10:
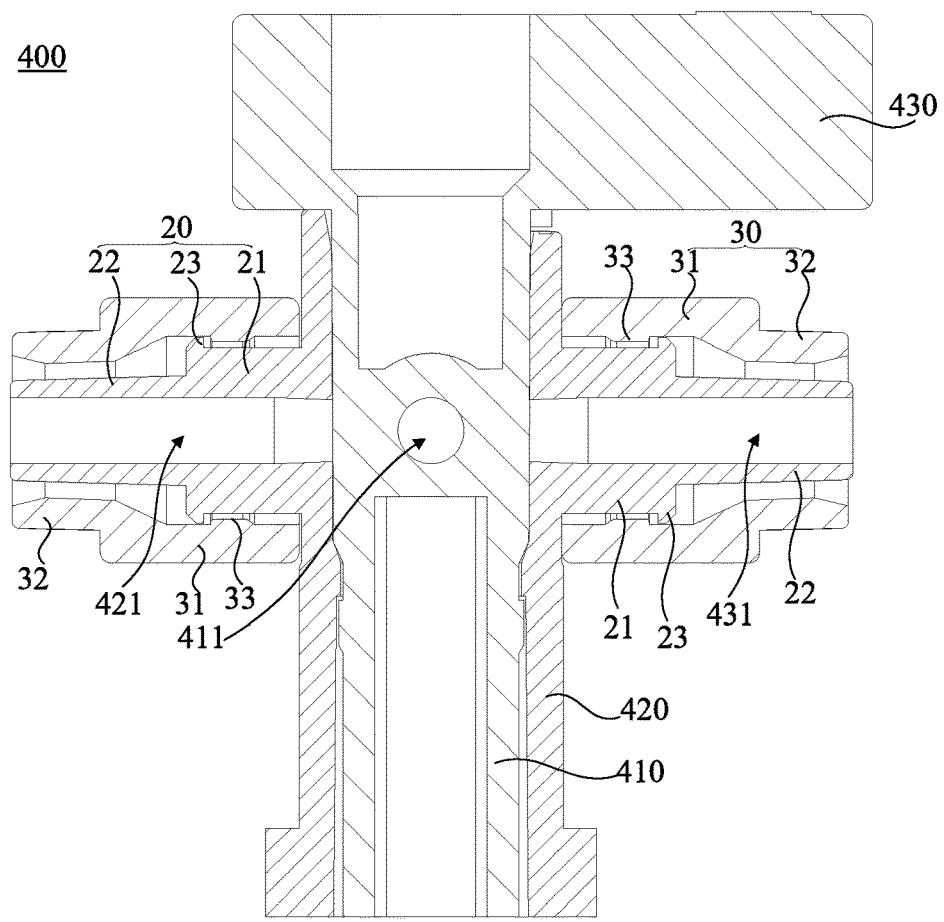
FIG. 10 is a sectional view taken along a line A-A in FIG. 9.

Referring to FIG. 4 to FIG. 6, the heating tank 100 is a non-deformable tank. The heating tank 100 includes a tank body 110 and a cover body 120. The tank body 110 is hollow, and one end of the tank body 110 is opened to form an open end. The cover body 120 is disposed on the open end of the tank body 110. The cover body 120 and the tank body 110 together form the liquid storage cavity 100*a*, and the liquid storage cavity 100*a* is configured to store liquid. During use, the tank body 110 is configured to be placed on the electromagnetic induction heating device, and the electromagnetic induction heating device is configured to heat the tank 100 body to indirectly heat liquid in the liquid storage cavity 100*a*, so that a non-direct contact heating method is achieved, the medicinal solution can be prevented from being polluted, thereby meeting the aseptic requirements.

Specifically, in the present embodiment, the tank body 110 includes a tank shell 111 and a base 112. The base 112 is disposed on the bottom of the tank body 110. The tank shell 111 is made of plastic materials, and the base 112 is made of metal materials. The base 112 and the tank shell 111 are integrally formed by an injection molding. Therefore, the entire heating tank 100 has a low manufacturing cost and a simple manufacturing process, and is convenient to use as a disposable product. When an electromagnetic induction coil is energized, only the bottom of the heating tank 100 is heated, and the liquid in the heating tank 100 is uniformly heated by utilizing the natural convection action of the liquid in the heating tank 100. For example, the base 112 may be made of medical grade 304 stainless steel.

Certainly, in other embodiments, the tank body 110 has the bottom, which is away from the open end. Only the bottom of the tank body 110 is made of metal materials, and the rest of the tank body 110 is made of plastic materials. Alternatively, the tank body 110 may be made of metal materials as a whole. Therefore, when the electromagnetic induction coil is energized to heat the heating tank 100, the liquid in the heating tank 100 is heated indirectly.

Specifically, in the present embodiment, the heating tank 100 further includes an air filter 130 and a sealing cap 140.

A matching joint 150 is formed on the cover body 120, and the air filter 130 is in communication with the liquid storage cavity 100*a* through the matching joint 150. The sealing cap 140 is capable of sealing the air filter 130. The air filter 130 is mainly used to prevent bacteria or particles in the air from directly entering the liquid storage cavity 100*a* to cause the contamination of the medicinal solution when the air pressure in the tank body 110 is in communication with the atmospheric pressure. Specifically, the air filter 130 includes a multilayer air filter element for filtering external air to prevent the bacteria carried in the air from entering the liquid storage cavity 100*a*. For example, the air filter 130 includes a housing made of ABS and AS materials, and a filter membrane made of PP and PTFE materials. A filtration rate of 0.5 micron particles in the air with the air filter 130 is greater than 90%.

Specifically, the air filter 130 is connected to the matching joint 150 by a threaded engagement. The air filter 130 is provided with a through hole. The air filter element is located in the through hole. The sealing cap 140 is rotatably disposed on the air filter 130 and can seal the through hole. The sealing cap 140 is mainly used to adjust the pressure in the liquid storage cavity 100*a*. Since the tank body 110 is made of a non-deformable material, when the volume of the medicinal solution in the tank body 110 is changed, the pressure in the tank body 110 is changed. For example, when the medicinal solution is injected into the heating tank 100, the pressure in the tank body 110 increases with the increase of the medicinal solution, which may eventually cause the pressure in the tank body 110 to be equal to the pressure for injecting the medicinal solution, so that no more medicinal solution can be injected. Alternatively, when the tank body 110 is fully loaded, a negative pressure may be generated in the liquid storage cavity 100*a* after the medicinal solution in the liquid storage cavity 100*a* is extracted. At this time, the medicinal solution in the bladder can be sucked out by adjusting the negative pressure. Specifically, in the present embodiment, the heating tank 100 further includes a first temperature measuring assembly 160, which is used to accurately measure the temperature of the liquid in the liquid storage cavity 100*a* to monitor the temperature of the liquid in real time. The first temperature measuring assembly 160 includes a first temperature sensor and a first hollow pipe. The first temperature sensor has a first probe end extending into the first hollow pipe and located on an end of the first hollow pipe. One end of the first hollow pipe extends into the liquid storage cavity 100*a* and is disposed proximate to the bottom of the tank body 110. Therefore, the first temperature measuring assembly 160 can always be in contact with the liquid to ensure that the actual temperature of the liquid is measured, rather than the temperature of the air leaving the liquid level. However, there is a certain distance between the end of the first temperature measuring assembly 160 and the bottom of the tank body 110, so that the phenomenon that the first temperature measuring assembly 160 generates heat or is interfered by the electromagnetic induction heating device to cause inaccurate measurement is avoided.

The heating tank 100 further includes a stirring impeller 170, which is located in the liquid storage cavity 100*a* and below the liquid return pipeline 104, and is capable of rotating under the action of the liquid flowing back to the liquid storage cavity 100*a* through the liquid return pipeline 104. Specifically, the stirring impeller 170 is provided on a side of the cover body 120 facing the tank body 110 by a support frame 180. The stirring impeller 170 includes a stirring blade 171 and a rotating shaft 172. Both ends of the rotating shaft 172 are rotatably disposed on the support frame 180, and the stirring blade 171 is fixed on the rotating shaft 172. Certainly, in other embodiments, the rotating shaft 172 may also be fixed on the support frame 180, and the stirring blade 171 may rotate relative to the rotating shaft 172.

When the liquid storage cavity 100a is filled with liquid, the electromagnetic induction heating device indirectly heats the liquid through heating the tank body 110. Because the base 112 of the tank body 110 or the bottom of the tank body 110 is made of stainless steel, the heat is transferred to the liquid from the bottom of the tank body 110. The density of the liquid decreases after the liquid is heated, the liquid will naturally float upwards, while the liquid with a low temperature above will sink, thereby resulting in a natural convection process. In this process, the stirring impeller 170 is also rotated, thereby playing a role of stirring.

Referring to FIG. 1 and FIG. 2 again, the circulation pipeline for intracavity hyperthermic perfusion 10 further includes a pressure measuring assembly 300, which is connected in series to the liquid outlet pipeline 102 and is located behind a station of the circulation pump 200. The pressure measuring assembly 300 is configured to measure a pressure in the liquid outlet pipeline 102 behind the station of the circulation pump 200, so that the pressure in the liquid outlet pipeline 102 can be monitored, which may avoid the damage to the bladder caused by the excessive pressure, or avoid that the medicinal solution cannot enter the bladder due to the too little pressure.

Specifically, the pressure measuring assembly 300 includes a pressure measuring extension pipe 310, a pressure measuring valve 320, and a pressure measuring protection cap 330. The pressure measuring extension pipe 310 is connected in series to the liquid outlet pipeline 102 and is located behind the station of the circulation pump 200. The pressure measuring valve 320 is configured to control opening and closing of the pressure measuring extension pipe 310, and the pressure measuring protection cap 330 is sleeved on one end of the pressure measuring extension pipe 310. The pressure of the medicinal solution flowing out of the circulation pump 200 in the liquid outlet pipeline 102 can be monitored in real time by externally connecting the pressure measuring extension pipe 310 to the pressure measuring sensor.

One end of the liquid inlet pipeline 101, which is configured to be in communication with the medicinal solution bag, is provided with a contact pin 108. The contact pin 108 is used to be inserted into the medicinal solution bag to smoothly introduce the medicinal solution in the medicinal solution bag into the liquid inlet pipeline 101. Optionally, a protection cover 109 can also be sleeved on the contact pin 108 to cover the contact pin 180, which not only prevents the contact pin 108 from accidentally damaging the operator, but also prevents external debris and dust from entering the liquid inlet pipeline 101 through the contact pin.

Referring to FIG. 2 and FIG. 7 to FIG. 10 together, the circulation pipeline for intracavity hyperthermic perfusion 10 further includes a two-way valve 400, which is connected in series to the liquid inlet pipeline 101 and is configured to control opening and closing of the liquid inlet pipeline 101. The two-way valve 400 includes a valve main body, and the valve main body includes a valve core 410 and a valve body 420. The valve core 410 is provided with a liquid through hole 411. For example, the liquid through hole 411 extends in a radial direction of the valve core 410. Certainly, in other embodiments, the liquid through hole 411 may not only be limited to extend in the radial direction, but may also be a curved through hole or the like, for example.

At least one end of the valve body 420 is opened and an interior of the valve body 420 is hollow to form a receiving cavity. The valve core 410 has a substantially cylindrical shape, and the receiving cavity is substantially a circular hole, which may facilitate the rotation of the valve core 410 in the receiving cavity. A first liquid inlet channel 421 and a first liquid outlet channel 431 which are in communication with the receiving cavity are formed on a side wall of the valve body 420. One end of the valve core 410 extends into the receiving cavity, and is rotatable relative to the valve body 420, so that the liquid through hole 411 can be or cannot be in communication with the first liquid inlet channel 421 and the first liquid outlet channel 431.

Specifically, in the present embodiment, an outer side wall of one end of the valve core 410 extending into the receiving cavity is recessed to form a positioning groove, and an inner side wall of the receiving cavity protrudes to form a positioning convex ring matched with the positioning groove.

Therefore, the positions of the valve core 410 and the valve body 420 can be positioned by the matching of the positioning groove and the positioning convex ring, which may prevent the valve core 410 from excessively extending into the valve body 420.

Specifically, in the present embodiment, the other end of the valve core 410 extends out of the receiving cavity, and the other end of the valve core 410 protrudes to form an operation handle 430. The operation handle 430 can be manually operated to rotate the valve core 410 relative to the valve body 420. Certainly, in other embodiments, the valve core 410 can also be driven to rotate relative to the valve body 420 by a motor, thereby achieving the purpose of automatic on-off.

Figure 11:
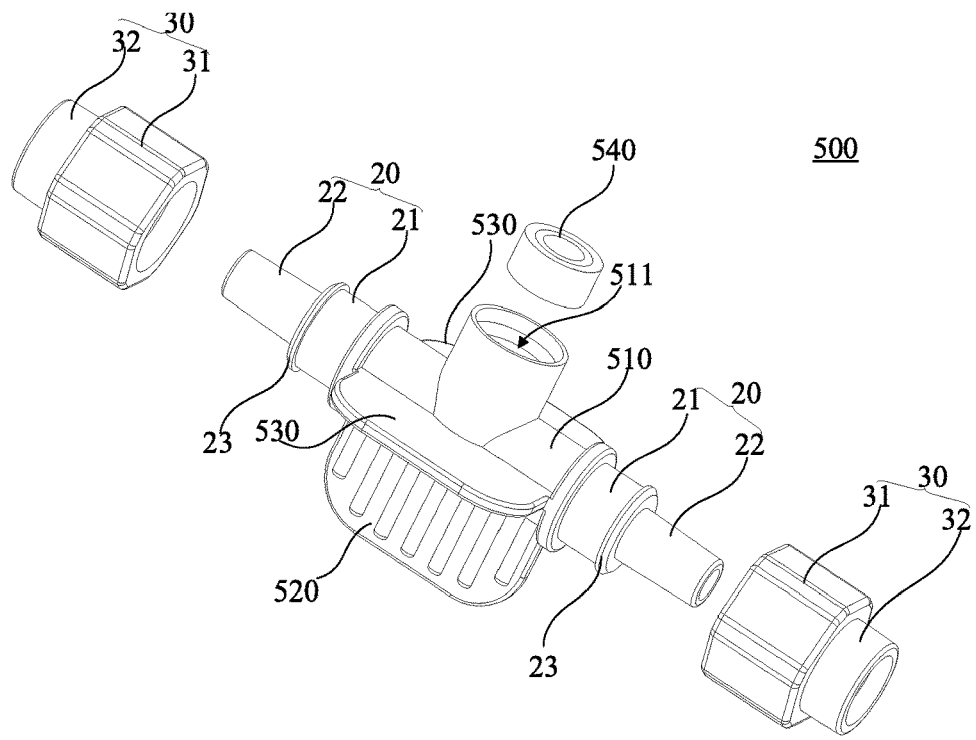
FIG. 11 is a schematic exploded view of a dosing joint in accordance with an embodiment.
Figure 12:
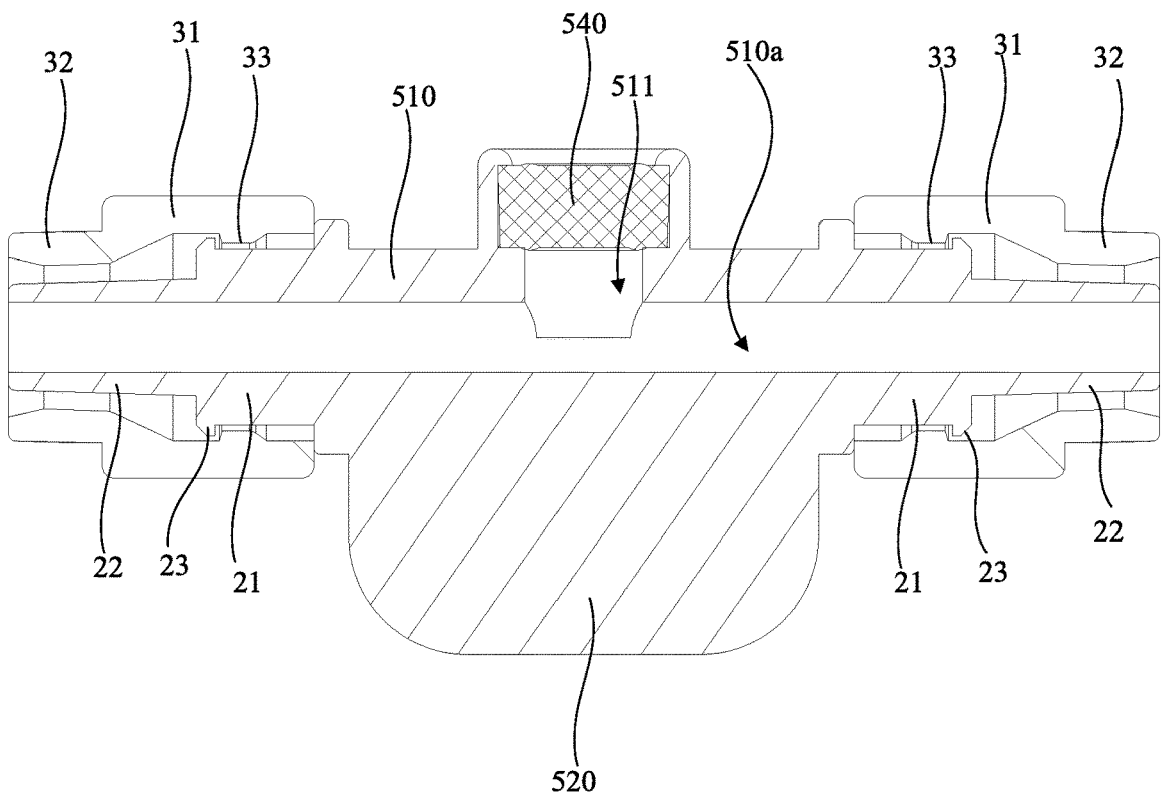
FIG. 12 is a sectional view of the dosing joint of FIG. 11 after assembly.

Referring to FIG. 2, FIG. 11, and FIG. 12 together, the circulation pipeline for intracavity hyperthermic perfusion 10 further includes a dosing joint 500, which is connected in series to the liquid inlet pipeline 101, and chemotherapy drugs and the like can be injected into the liquid inlet pipeline 101 through the dosing joint 500. The dosing joint 500 includes a dosing pipe body 510, a handle 520, and a protection flap 530. An infusion channel 510a in communication with the liquid inlet pipeline 101 is formed inside the dosing pipe body 510. A dosing hole 511 in communication with the infusion channel 510a is formed on a side wall of the dosing pipe body 510. The dosing pipe body 510 is provided with a dosing soft plug 540 for sealing the dosing hole 511 to prevent air or other dust from entering the pipeline system. Specifically, the dosing soft plug 540 may be a silicone plug. Certainly, in other embodiments, the dosing soft plug 540 may also be made of other soft materials, as long as the dosing soft plug 540 is capable of sealing the dosing hole 511 and being inserted by a needle tip of a syringe.

The handle 520 is disposed on an outer side wall of the dosing pipe body 510 and is spaced apart from the dosing hole 511. The protection flap 530 is disposed on the outer side wall of the dosing pipe body 510 and is located between the dosing hole 511 and the handle 520 to form a protection wall. Therefore, when one hand holds the handle 520 and the other hand holds the syringe and the needle tip of the syringe is inserted into the dosing soft plug 540, the protection flap 530 forms a protection wall between the hand and the needle tip, which may effectively prevent the needle tip from hurting the hands due to careless operation.

Figure 13:
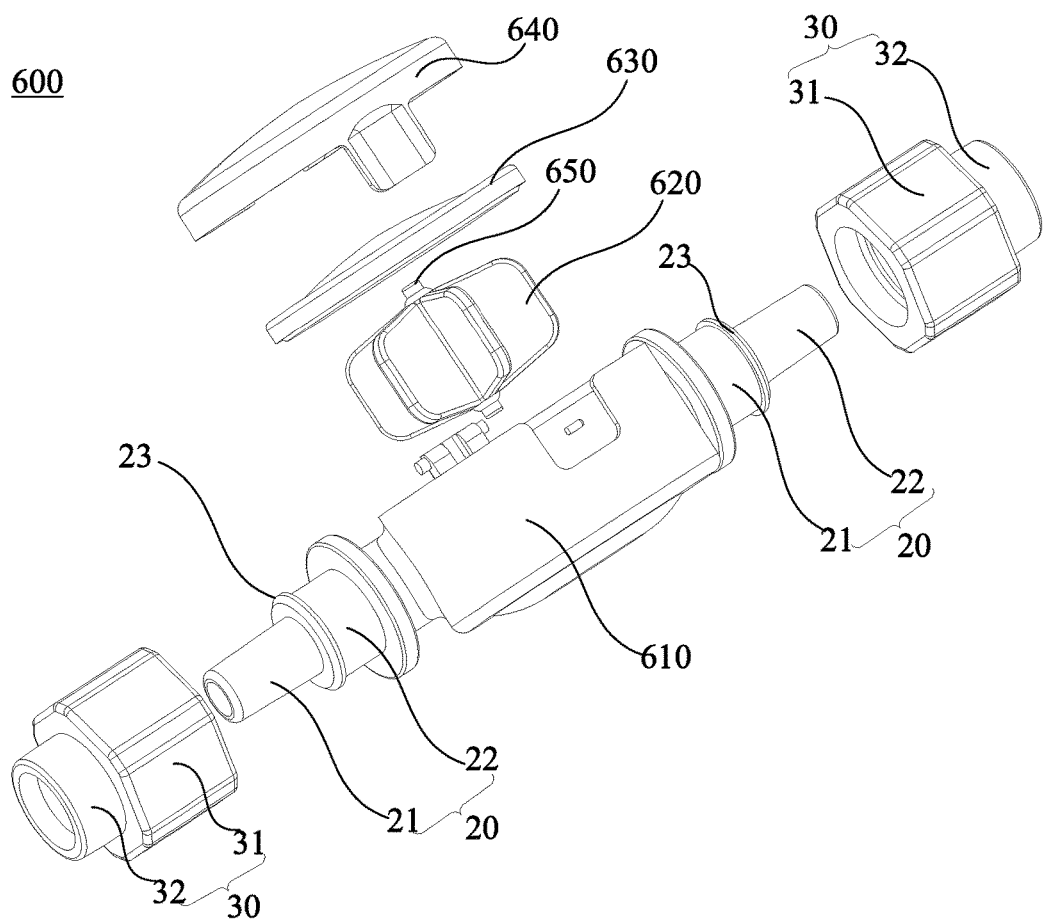
FIG. 13 is a schematic exploded view of a cavity inlet flow indicator in accordance with an embodiment.
Figure 14:
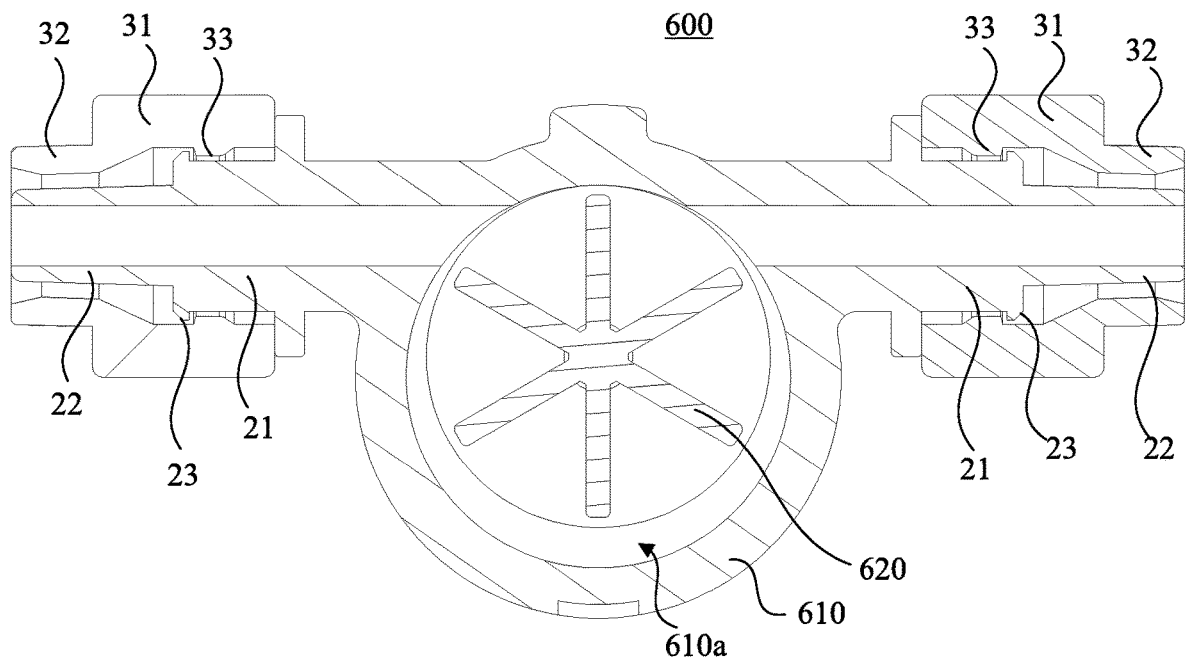
FIG. 14 is a sectional view of the cavity inlet flow indicator of FIG. 13 after assembly.

Referring to FIG. 3, FIG. 13 and FIG. 14, the circulation pipeline for intracavity hyperthermic perfusion 10 further includes a cavity inlet flow indicator 600, which is connected in series to the liquid outlet pipeline 102. For example, in the present embodiment, the cavity inlet flow indicator 600 is located behind the station of the pressure measuring assembly 300. The cavity inlet flow indicator 600 may be more beneficial for observing a flow status of the liquid in the pipeline system.

Specifically, the cavity inlet flow indicator 600 includes a seating 610, an impeller 620, a transparent cover body 630, and a light-shielding upper cover 640. The seating 610 is formed with an impeller cavity 610a that is in communication with the liquid outlet pipeline 102. The impeller 620 is rotatably disposed on the seating 610 through a rotating shaft 650 and is located in the impeller cavity 610a. The transparent cover body 630 is disposed on the seating 610 to seal the impeller cavity 610a. The light-shielding upper cover 640 is coverably disposed on the seating 610, and is capable of covering the transparent cover body 630.

The seating 610 is made of a light-shielding material, and the transparent cover body 630 may be made of a transparent material, such as transparent plastic or transparent glass. When the liquid enters the impeller cavity 610a, the impeller 620 is washed due to the continuity of the liquid. The impeller 620 may rotate under the action of the flowing liquid, and whether the liquid is in a flowing state can be known by observing whether the impeller 620 rotates through the transparent cover 630.

The impeller 620 is eccentrically disposed with respect to the impeller cavity 610a to accommodate a lower flow velocity. For example, in the case of that a flow indicator is applied to a bladder circulation hyperthermic perfusion device, during the treatment, the flow velocity in the pipeline system is generally between 50 ml/min and 200 ml/min, in most cases the flow velocity is lower than 150 ml/min. Such flow velocity is relatively low, thereby requiring increased sensitivity to rotation of the impeller 620.

Figure 15:
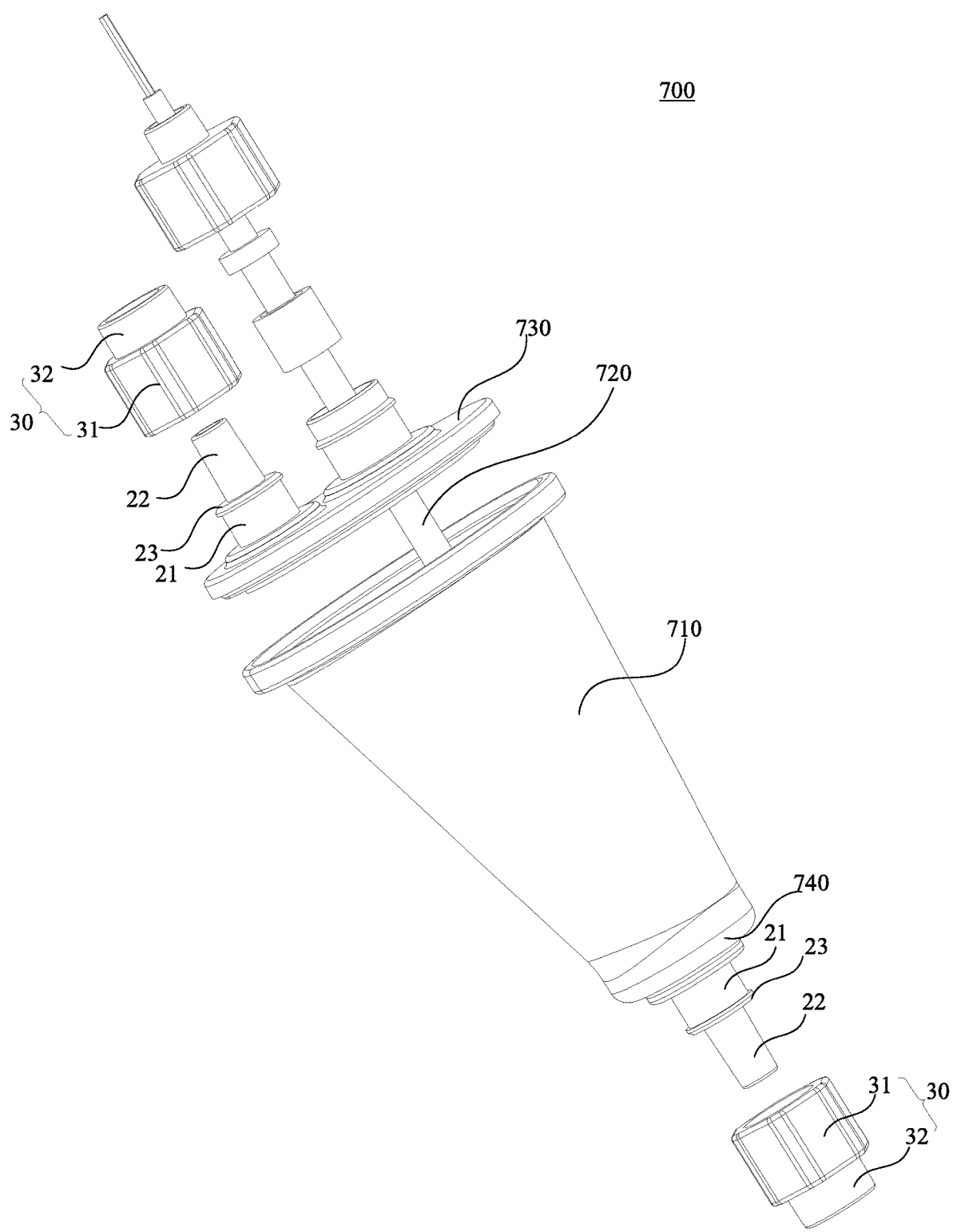
FIG. 15 is a schematic exploded view of a cavity inlet thermometer in accordance with an embodiment.
Figure 16:
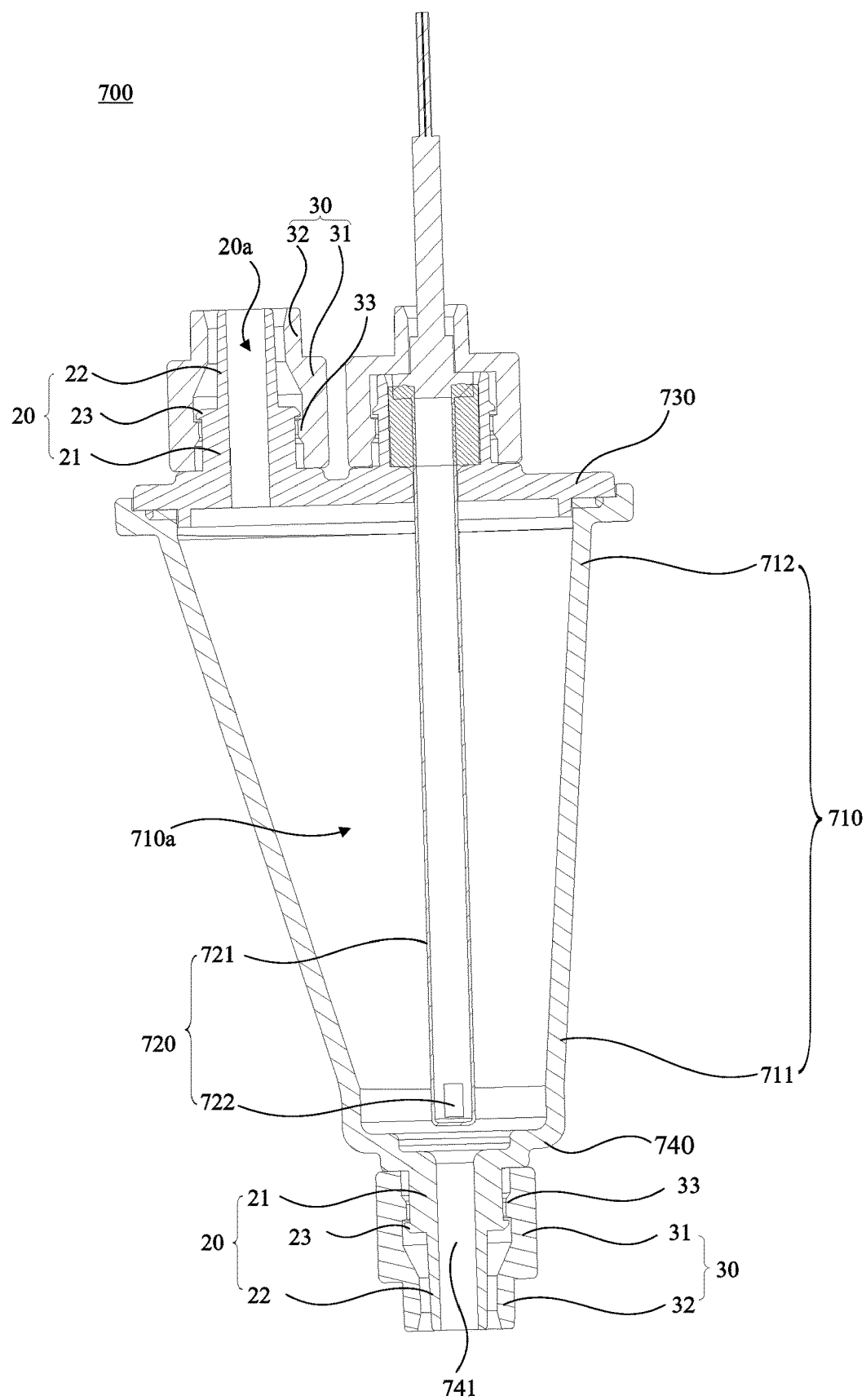
FIG. 16 is a sectional view of the cavity inlet thermometer of FIG. 15 after assembly.

Referring to FIG. 3 and FIG. 15 to FIG. 16 together, the circulation pipeline for intracavity hyperthermic perfusion 10 further includes a cavity inlet thermometer 700. The cavity inlet thermometer 700 is connected in series to the liquid outlet pipeline 102 and is configured to measure the temperature of the liquid flowing in the liquid outlet pipeline 102 in real time and truthfully, so as to monitor the true temperature of the liquid entering the bladder. For example, in the present embodiment, the cavity inlet thermometer 700 is located behind the station of the cavity inlet flow indicator 600.

The cavity inlet thermometer 700 includes a first liquid storage housing 710, a second temperature measuring assembly 720, a first cavity inlet end cover 730, and a second cavity inlet end cover 740. An interior of the first liquid storage housing 710 is hollow to form a first liquid storage cavity 710a in communication with the liquid outlet pipeline 102. The first liquid storage housing 710 includes a first small-diameter end 711 and a first large-diameter end which are oppositely disposed. An inner diameter of the first small-diameter end 711 is less than an inner diameter of the first large-diameter end 712.

The second temperature measuring assembly 720 includes a second hollow pipe 721 and a second temperature sensor. The second temperature sensor has a second probe end 722 extending into the second hollow pipe 721 and located at an end of the second hollow pipe 721. The first cavity inlet end cover 730 covers the first large-diameter end 712 of the first liquid storage housing 710, and the second cavity inlet end cover 740 is disposed on the first small-diameter end 711 of the first liquid storage housing 710. The second hollow pipe 721 extends into the first liquid storage cavity 710a from the first cavity inlet end cover 730 and is adjacent to a first liquid inlet through hole 741 on the second cavity inlet end cover 740.

If the second probe end 722 of the second temperature sensor is too close to the side wall of the first liquid storage housing 710 or directly adheres to the side wall of the first liquid storage housing 710, the measured temperature will be 1° C. to 2° C. lower than the actual temperature of the liquid because of the inevitable heat dissipation of the first liquid storage housing 710. If the second probe end 722 of the second temperature sensor is located in the middle of the first liquid storage cavity 710a, since there is a dead water zone or the flow velocity less than the actual flow velocity of the liquid in the pipeline, the measured temperature will also be 1° C. lower than the actual temperature of the liquid. Therefore, in the present embodiment, the second probe end 722 is disposed adjacent to the first liquid inlet through hole, but is not in direct contact with the first liquid storage housing 710.

Referring to FIG. 3, the circulation pipeline for intracavity hyperthermic perfusion 10 further includes a cavity outlet thermometer 700'. The cavity outlet thermometer 700' is connected in series to the liquid return pipeline 102 and is configured to measure the temperature of the liquid flowing from the bladder through the cavity outlet pipeline 106 in real time and truthfully. Specifically, the structure of the cavity outlet thermometer 700' is substantially the same as the structure of the cavity inlet thermometer 700.

The cavity outlet thermometer 700' includes a second liquid storage housing, a third temperature measuring assembly, a first cavity outlet end cover, and a second cavity outlet end cover. An interior of the second liquid storage housing is hollow to form a second liquid storage cavity in communication with the liquid return pipeline. The second liquid storage housing includes a second small-diameter end and a second large-diameter end which are oppositely disposed. An inner diameter of the second small-diameter end is less than an inner diameter of the second large-diameter end.

The third temperature measuring assembly includes a third hollow pipe and a third temperature sensor. The third temperature sensor has a third probe end extending into the third hollow pipe and located at an end of the third hollow pipe. The first cavity outlet end cover covers the second large-diameter end of the second liquid storage housing, and the second cavity outlet end cover is disposed on the second small-diameter end of the second liquid storage housing. The third hollow pipe extends into the second liquid storage cavity from the first cavity outlet end cover and is adjacent to a second liquid inlet through hole on the second cavity outlet end cover.

If the third probe end of the third temperature sensor is too close to the side wall of the second liquid storage housing or directly adheres to the side wall of the second liquid storage housing, the measured temperature will be 1° C. to 2° C. lower than the actual temperature of the liquid because of the inevitable heat dissipation of the second liquid storage housing. If the third probe end of the third temperature sensor is located in the middle of the second liquid storage cavity, since there is a dead water zone or the flow velocity less than the actual flow velocity of the liquid in the pipeline, the measured temperature will also be 1° C. lower than the actual temperature of the liquid. Therefore, in the present embodiment, the third probe end is disposed adjacent to the second liquid inlet through hole, but is not in direct contact with the second liquid storage housing.

Figure 17:
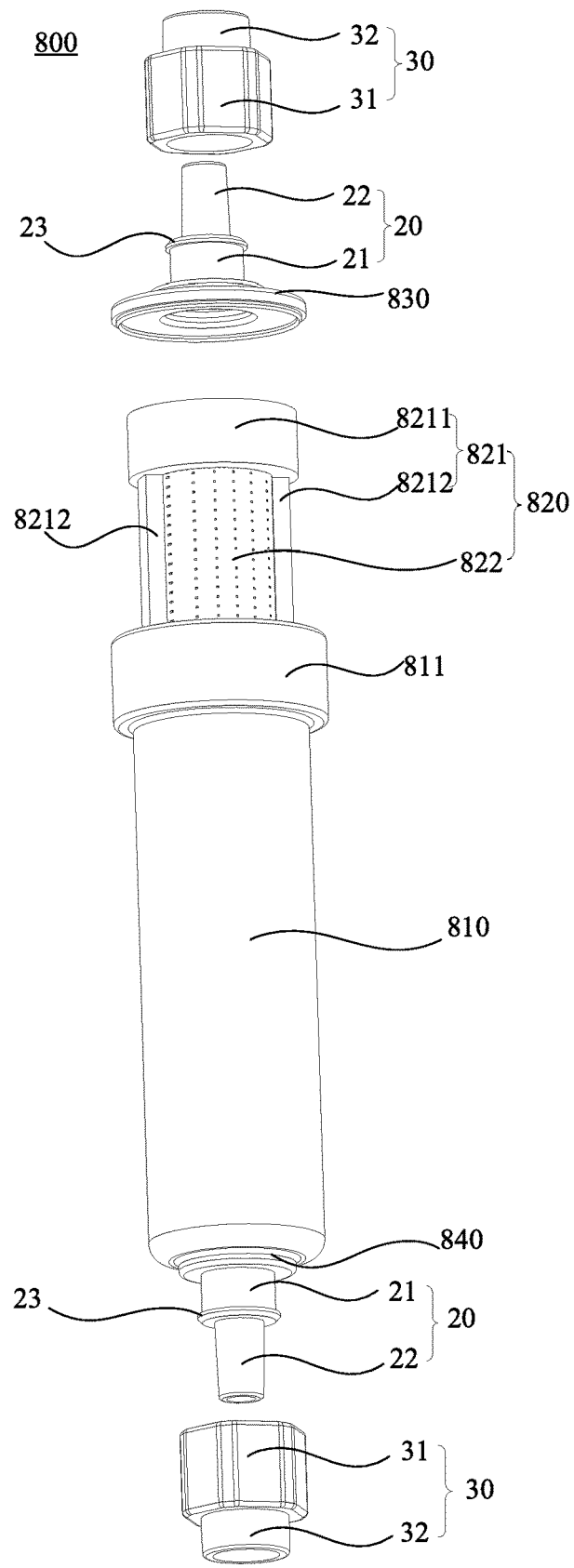
FIG. 17 is a schematic exploded view of a filter in accordance with an embodiment.
Figure 18:
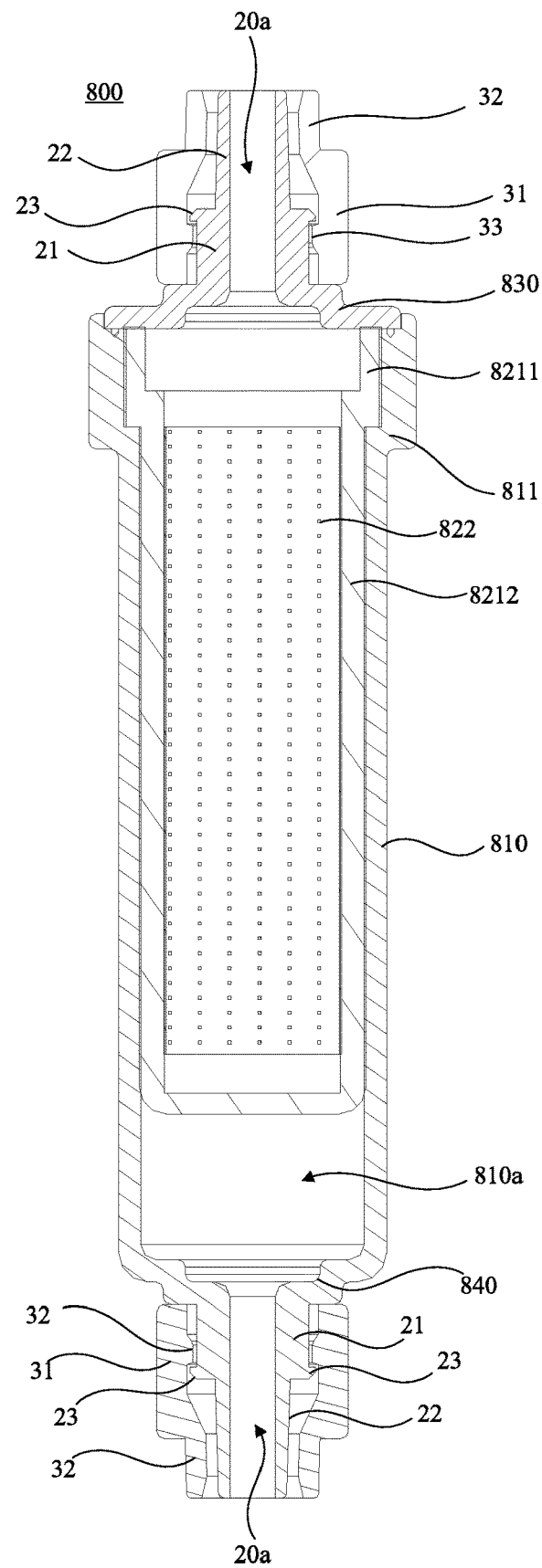
FIG. 18 is a sectional view of the filter of FIG. 17 after assembly.

Referring to FIG. 2, FIG. 17, and FIG. 18 together, the circulation pipeline for intracavity hyperthermic perfusion 10 further includes a filter 800 connected in series to the liquid return pipeline 104. For example, the filter 800 is located behind the station of the cavity outlet thermometer 700'. The filter 800 can filter the medicinal solution flowing out of the bladder to prevent dropped tissues from damaging other components.

Specifically, the filter 800 includes a housing 810, a filter element 820, an upper cover 830, and a lower cover 840. The housing 810 is formed with a filter element cavity 810a that is in communication with the liquid return pipeline 104. The filter element 820 is received in the filter element cavity 810a and is configured to filter the medicinal solution. Specifically, the housing 810 may be hollow cylindrical. The filter element 820 includes a holder 821 and a filter screen 822, and the filter screen 822 is disposed on the holder 821. The upper cover 830 is disposed on one end of the housing 810, and the lower cover 840 is disposed on the other end of the housing 810.

A side wall of one end of the housing 810 protrudes outward to form a positioning step 811. The holder 821 includes a positioning cylinder 8211 and at least two reinforcing ribs 8212. The positioning cylinder 8211 abuts against the positioning step 811. One end of each reinforcing rib 8212 is disposed on the positioning cylinder 8211. The reinforcing ribs 8212 are distributed at intervals in the radial direction. When the filter element 820 is assembled into the housing 810, one end of the filter element 820 extends into the filter element cavity 810a until the positioning cylinder 8211 abuts against the positioning step 811 to complete the assembly, so that the assembly and disassembly are facilitated.

Referring to FIG. 2, the circulation pipeline for intracavity hyperthermic perfusion 10 further includes a cavity outlet flow indicator 600' that is connected in series to the liquid return pipeline 104. For example, in the present embodiment, the cavity outlet flow indicator 600' is connected in series behind the station of the filter 800. The structure of the cavity outlet flow indicator 600' is substantially the same as the structure of the cavity inlet flow indicator 600.

Specifically, the cavity outlet flow indicator 600' includes a seating 610, an impeller 620, a transparent cover body 630, and a light-shielding upper cover 640. The seating 610 is formed with an impeller cavity 610a in communication with the liquid outlet pipeline 104. The impeller 620 is rotatably disposed on the seating 610 through a rotating shaft and is located within the impeller cavity 610a. The transparent cover body 630 is disposed on the seating 610 to seal the impeller cavity 610a.

The light-shielding upper cover 640 is coverably disposed on the seating 610 and is capable of covering the transparent cover body 630.

The seating 610 is made of a light-shielding material, and the transparent cover body 630 may be made of a transparent material, such as transparent plastic or transparent glass. When the liquid enters the impeller cavity 610a, the impeller 620 is washed due to the continuity of the liquid. The impeller 620 may rotate under the action of the flowing liquid, and whether the liquid is in a flowing state can be known by observing whether the impeller 620 rotates through the transparent cover 630.

The impeller 620 is eccentrically disposed with respect to the impeller cavity 610a to accommodate a lower flow velocity. For example, in the case of that a flow indicator is applied to a bladder circulation hyperthermic perfusion device, during the treatment, the flow velocity in the pipeline system is generally between 50 ml/min and 200 ml/min, in most cases the flow velocity is lower than 150 ml/min. Such flow velocity is relatively low, thereby requiring increased sensitivity to rotation of the impeller 620.

Referring to FIG. 2, the circulation pipeline for intracavity hyperthermic perfusion 10 further includes a flow regulating valve 900, which is connected in series to the liquid return pipeline 104. For example, in the present embodiment, the flow regulating valve 900 is located behind the station of the cavity outlet flow indicator, and is configured to regulate a flow velocity of the medicinal solution in the liquid return pipeline 104.

Specifically, the liquid inlet pipeline 101, the liquid outlet pipeline 102, the pre-filling pipeline 103, the cavity inlet pipeline 105, the cavity outlet pipeline 106, and the liquid return pipeline 104 can be flexible pipes made of soft materials. The flexible pipe may also have light-shielding properties to meet the requirements that certain drugs for bladder chemotherapy need to be shielded from light.

The two-way valve 400, the dosing joint 500, the pressure measuring assembly 300, the cavity inlet flow indicator 600, the cavity inlet thermometer 700, the cavity outlet thermometer 700', the filter 800, the cavity outlet flow indicator 600', and the flow regulating valve 900 can be connected in series to the pipeline system through a pure physical connection method in which a joint 20 and a locking sleeve 30 are matched, which may prevent the residue of an adhesive.

Specifically, a channel 20a is formed on the joint 20, and the liquid is in communication with the pipeline system through the channel 20a. The joint 20 includes a matching section 21 and a connecting section 22. A first protrusion 23 is formed on an outer side wall of the matching section 21. An outer side wall of the connecting section 22 is a conical surface. The locking sleeve 30 includes a first locking section 31 and a second locking section 32. A second protrusion 33 matched with the first protrusion 23 is formed on an inner side wall of the first locking section 31. An inner side wall of the second locking section 32 protrudes to form a pressing portion. The flexible pipe is compressed between the pressing portion and the connecting section 22.

When the locking sleeve 30 is matched with the joint, the locking sleeve 30 is sleeved on the flexible pipes in advance, and then one end of the flexible pipe is sleeved on the connecting section 22 of the joint. The flexible pipe is stretched by the connecting section 22 when being sleeved on the connecting section 22. The locking sleeve 30 is moved until the second protrusion 33 on the inner side wall of the first locking sleeve 30 passes through the first protrusion 23 on the outer side wall of the matching section 21, and the pressing portion on the inner side wall of the second locking section 32 has a certain pressing effect on the flexible pipe, so that the flexible pipe can be compressed between the connecting section 22 and the second locking section 32, which may prevent the flexible pipe from detaching from the joint.

The above-mentioned circulation pipeline for intracavity hyperthermic perfusion 10 has at least the following advantages:

The contact pin is inserted into the medicinal solution bag, and the valve core 410 of the two-way valve 400 is rotated to make the two-way valve 400 in an open state. The medicinal solution in the medicinal solution bag enters the liquid storage cavity 100a of the heating tank 100 through the liquid inlet pipeline 101, and the chemotherapeutic drug and the like can be injected into the liquid inlet pipeline 101 through the dosing joint 500. When the amount of the medicinal solution in the heating tank 100 reaches a set value, the two-way valve 400 is closed, and the liquid inlet pipeline 101 is in a closed state, and the medicinal solution in the heating tank 100 is pre-heated by the electromagnetic induction heating device until the pre-heating temperature is reached.

The pre-filling valve 1031 is opened, and the cavity inlet valve 1051 and the cavity outlet valve 1061 are closed, the medicinal solution is extracted out of the liquid storage cavity 100a under the action of the circulation pump 200. The pressure measuring assembly 300 is externally connected to the pressure measuring sensor and measures the pressure of the liquid in the liquid outlet pipeline 102. The medicinal solution passes through the cavity inlet flow indicator 600 and cavity inlet thermometer 700 in the liquid outlet pipeline 102, then is introduced into the pre-filling pipeline 103, and then flows back to the heating tank 100 through the cavity outlet thermometer 700', the filter 800, the cavity outlet flow indicator 600', and the flow regulating valve 900 in the liquid return pipeline 104. The medicinal solution flows back to the heating tank 100 through the liquid outlet pipeline 102, the pre-filling pipeline 103, and the liquid return pipeline 104, so that the air in the pipeline system can be exhausted in advance to avoid causing inflammation.

Then, the pre-filling valve 1031 is closed, the cavity inlet valve 1051 and the cavity outlet valve 1061 are opened, the medicinal solution is extracted out of the liquid storage cavity 100a again under the action of the circulation pump 200, and then enters the bladder through the liquid outlet pipeline 102 and the cavity inlet pipeline 105. After that, the medicinal solution flows out of the bladder and flows back to the heating tank 100 through the cavity outlet pipeline 106 and the liquid return pipeline 104. During the circulation process of the medicinal solution, the heating tank 100 can continuously heat the medicinal solution until the set temperature is reached, which achieves the purpose of simultaneous circulating and heating, thereby preventing the temperature of the medicinal solution from being rapidly heated at the beginning and avoiding the contraction or spasm of the bladder.

The above-mentioned embodiments only express several implementation manners of the present disclosure, and their descriptions are more specific and detailed, but they cannot be understood as limiting the scope of the invention disclosure. It should be noted that, for those of ordinary skill in the art, without departing from the concept of the present disclosure, several modifications and improvements can be made, which all belong to the protection scope of the present disclosure. Therefore, the protection scope of the invention disclosure shall be subject to the appended claims.

What is claimed is:

1. A circulation pipeline for intracavity hyperthermic perfusion, comprising:
a heating tank, the heating tank being hollow to form a liquid storage cavity, the liquid storage cavity being configured to store a medicinal solution, wherein the heating tank comprises a tank body and a cover body, the tank body is hollow, one end of the tank body is opened to form an open end, the cover body is disposed on the open end of the tank body, the cover body and the tank body together form the liquid storage cavity, the tank body is configured to be placed on an electromagnetic induction heating device, and the electromagnetic induction heating device is configured to heat the tank body to indirectly heat liquid in the liquid storage cavity;
a liquid inlet pipeline, one end of the liquid inlet pipeline being in communication with the liquid storage cavity, and the other end of the liquid inlet pipeline being configured to be in communication with a medicinal solution bag;
a liquid outlet pipeline, one end of the liquid outlet pipeline being in communication with the liquid storage cavity;
a circulation pump connected in series to the liquid outlet pipeline and configured to extract the medicinal solution in the liquid storage cavity;
a pre-filling pipeline, one end of the pre-filling pipeline being in communication with the other end of the liquid outlet pipeline;
a liquid return pipeline, one end of the liquid return pipeline being in communication with the other end of the pre-filling pipeline, and the other end of the liquid return pipeline being in communication with the liquid storage cavity;
a cavity inlet pipeline, one end of the cavity inlet pipeline being in communication with the other end of the liquid outlet pipeline, and the other end of the cavity inlet pipeline being in communication with a body cavity; and
a cavity outlet pipeline, one end of the cavity outlet pipeline being configured to be in communication with the body cavity, the other end of the cavity outlet pipeline being in communication with one end of the liquid return pipeline, and the pre-filling pipeline being connected in parallel with the cavity inlet pipeline and the cavity outlet pipeline.

2. The circulation pipeline for intracavity hyperthermic perfusion of claim 1, wherein the tank body comprises a tank shell and a base, the base is disposed on a bottom of the tank shell, the tank shell is made of plastic materials, and the base is made of metal materials, and the base and the tank shell are integrally formed by an injection molding; or
the tank body is made of metal materials as a whole; or
the tank body has a bottom away from the open end, and the bottom of the tank body is made of metal materials.

3. The circulation pipeline for intracavity hyperthermic perfusion of claim 1, wherein the heating tank further comprises an air filter and a sealing cap, a matching joint is formed on the cover body, the air filter is in communication with the liquid storage cavity through the matching joint, and the sealing cap is capable of sealing the air filter.

4. The circulation pipeline for intracavity hyperthermic perfusion of claim 1, wherein the heating tank further comprises a first temperature measuring assembly comprising a first temperature sensor and a first hollow pipe, the first temperature sensor has a first probe end extending into the first hollow pipe and located on an end of the first hollow pipe, and one end of the first hollow pipe extends into the liquid storage cavity and is disposed proximate to a bottom of the tank body.

5. The circulation pipeline for intracavity hyperthermic perfusion of claim 1, further comprising a pressure measuring assembly connected in series to the liquid outlet pipeline and located behind a station of the circulation pump, the pressure measuring assembly being configured to measure a pressure in the liquid outlet pipeline behind the station of the circulation pump.

6. The circulation pipeline for intracavity hyperthermic perfusion of claim 5, wherein the pressure measuring assembly comprises a pressure measuring extension pipe, a pressure measuring valve, and a pressure measuring protection cap, the pressure measuring extension pipe is connected in series to the liquid outlet pipeline and is located behind the station of the circulation pump, the pressure measuring valve is configured to control opening and closing of the pressure measuring extension pipe, and the pressure measuring protection cap is sleeved on one end of the pressure measuring extension pipe.

7. The circulation pipeline for intracavity hyperthermic perfusion of claim 1, further comprising:
a two-way valve connected in series to the liquid inlet pipeline, wherein the two-way valve is configured to control opening and closing of the liquid inlet pipeline, the two-way valve comprises a valve main body comprising a valve core and a valve body, the valve core is provided with a liquid through hole, at least one end of the valve body is opened and an interior of the valve body is hollow to form a receiving cavity, a first liquid inlet channel and a first liquid outlet channel which are in communication with the receiving cavity are formed on a side wall of the valve body, one end of the valve core extends into the receiving cavity, and the valve core is rotatable relative to the valve body, so that the liquid through hole is capable of being or being not in communication with the first liquid inlet channel and the first liquid outlet channel; and/or
a dosing joint connected in series to the liquid inlet pipeline, wherein the dosing joint comprises a dosing pipe body, a handle, and a protection flap, an infusion channel in communication with the liquid inlet pipeline is formed inside the dosing pipe body, a dosing hole in communication with the infusion channel is formed on a side wall of the dosing pipe body, the dosing pipe body is provided with a dosing soft plug configured to seal the dosing hole, the handle is disposed on an outer side wall of the dosing pipe body and is spaced apart from the dosing hole, and the protection flap is disposed on the outer side wall of the dosing pipe body and is located between the dosing hole and the handle to form a protection wall.

8. The circulation pipeline for intracavity hyperthermic perfusion of claim 1, further comprising:
a cavity inlet flow indicator connected in series to the liquid outlet pipeline, wherein the cavity inlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body; and/or
a cavity inlet thermometer connected in series to the liquid outlet pipeline, wherein the cavity inlet thermometer comprises a first liquid storage housing, a second temperature measuring assembly, a first cavity inlet end cover, and a second cavity inlet end cover, an interior of the first liquid storage housing is hollow to form a first liquid storage cavity in communication with the liquid outlet pipeline, the first liquid storage housing comprises a first small-diameter end and a first large-diameter end which are oppositely disposed, an inner diameter of the first small-diameter end is less than an inner diameter of the first large-diameter end, the second temperature measuring assembly comprises a second hollow pipe and a second temperature sensor, the second temperature sensor has a second probe end extending into the second hollow pipe and located on an end of the second hollow pipe, the first cavity inlet end cover covers the first large-diameter end of the first liquid storage housing, and the second cavity inlet end cover is disposed on the first small-diameter end of the first liquid storage housing, the second hollow pipe extends into the first liquid storage cavity from the first cavity inlet end cover and is adjacent to a first liquid inlet through hole on the second cavity inlet end cover.

9. The circulation pipeline for intracavity hyperthermic perfusion of claim 1, further comprising one or more of the following:
a cavity outlet thermometer connected in series to the liquid return pipeline, wherein the cavity outlet thermometer comprises a second liquid storage housing, a third temperature measuring assembly, a first cavity outlet end cover, and a second cavity outlet end cover, an interior of the second liquid storage housing is hollow to form a second liquid storage cavity in communication with the liquid return pipeline, the second liquid storage housing comprises a second small-diameter end and a second large-diameter end which are oppositely disposed, an inner diameter of the second small-diameter end is less than an inner diameter of the second large-diameter end, the third temperature measuring assembly comprises a third hollow pipe and a third temperature sensor, the third temperature sensor has a third probe end extending into the third hollow pipe and located on an end of the third hollow pipe, the first cavity outlet end cover covers the second large-diameter end of the second liquid storage housing, the second cavity outlet end cover is disposed on the second small-diameter end of the second liquid storage housing, and the third hollow pipe extends into the second liquid storage cavity from the first cavity outlet end cover and is adjacent to a second liquid inlet through hole on the second cavity outlet end cover;
a filter connected in series to the liquid return pipeline, wherein the filter comprises a housing, a filter element, an upper cover, and a lower cover, the housing is formed with a filter element cavity in communication with the liquid return pipeline, the filter element is received in the filter element cavity and is configured to filter the medicinal solution, the upper cover is disposed on one end of the housing, and the lower cover is disposed on the other end of the housing;
a cavity outlet flow indicator connected in series to the liquid return pipeline, wherein the cavity outlet flow indicator comprises a seating, an impeller, a transparent cover body, and a light-shielding upper cover, the seating is formed with an impeller cavity in communication with the liquid outlet pipeline, the impeller is rotatably disposed on the seating through a rotating shaft and is located within the impeller cavity, the transparent cover body is disposed on the seating to seal the impeller cavity, and the light-shielding upper cover is coverably disposed on the seating and is capable of covering the transparent cover body;
a flow regulating valve connected in series to the liquid return pipeline, wherein the flow regulating valve is configured to regulate a flow velocity of the medicinal solution in the liquid return pipeline.

\* \* \* \* \*